United States Patent
Kim et al.

(10) Patent No.: US 9,527,065 B2
(45) Date of Patent: Dec. 27, 2016

(54) CATALYST FOR GLYCERIN DEHYDRATION, PREPARATION METHOD THEREOF, AND PREPARATION METHOD OF ACROLEIN

(71) Applicant: LG CHEM, LTD., Seoul (KR)

(72) Inventors: Ji Yeon Kim, Daejeon (KR); Jun Seon Choi, Daejeon (KR); Joo Young Cheon, Daejeon (KR); Wang Rae Joe, Daejeon (KR)

(73) Assignee: LG Chem, Ltd., Seoul (JP)

( * ) Notice: Subject to any disclaimer, the term of this patent is extended or adjusted under 35 U.S.C. 154(b) by 0 days.

(21) Appl. No.: 14/653,670

(22) PCT Filed: Nov. 18, 2014

(86) PCT No.: PCT/KR2014/011079
§ 371 (c)(1),
(2) Date: Jun. 18, 2015

(87) PCT Pub. No.: WO2015/072813
PCT Pub. Date: May 21, 2015

(65) Prior Publication Data
US 2015/0343430 A1   Dec. 3, 2015

(30) Foreign Application Priority Data

Nov. 18, 2013  (KR) .................. 10-2013-0139992
Nov. 17, 2014  (KR) .................. 10-2014-0160193

(51) Int. Cl.
| | |
|---|---|
| *C07C 45/52* | (2006.01) |
| *B01J 29/46* | (2006.01) |
| *B01J 29/76* | (2006.01) |
| *B01J 29/072* | (2006.01) |
| *B01J 37/04* | (2006.01) |
| *B01J 27/053* | (2006.01) |
| *B01J 27/055* | (2006.01) |
| *B01J 29/42* | (2006.01) |
| *B01J 29/72* | (2006.01) |
| *B01J 37/00* | (2006.01) |
| *B01J 35/00* | (2006.01) |
| *B01J 29/40* | (2006.01) |
| *B01J 29/70* | (2006.01) |

(52) U.S. Cl.
CPC ............... *B01J 29/46* (2013.01); *B01J 27/053* (2013.01); *B01J 27/055* (2013.01); *B01J 29/072* (2013.01); *B01J 29/42* (2013.01); *B01J 29/7215* (2013.01); *B01J 29/7615* (2013.01); *B01J 37/0036* (2013.01); *B01J 37/04* (2013.01); *C07C 45/52* (2013.01); *B01J 29/40* (2013.01); *B01J 29/405* (2013.01); *B01J 29/7007* (2013.01); *B01J 29/7057* (2013.01); *B01J 35/0006* (2013.01); *B01J 2229/20* (2013.01)

(58) Field of Classification Search
CPC ......... C07C 45/52; C07C 45/512; B01J 29/46; B01J 26/072; B01J 37/04
USPC ..................... 568/486; 502/71, 218
See application file for complete search history.

(56) References Cited

U.S. PATENT DOCUMENTS

| | | | |
|---|---|---|---|
| 7,538,247 B2 * | 5/2009 | Craciun | ............... C07C 51/377 564/141 |
| 2011/0184216 A1 | 7/2011 | Sousa Fadigas et al. | |
| 2011/0224470 A1 | 9/2011 | Hulteberg et al. | |

FOREIGN PATENT DOCUMENTS

| | | |
|---|---|---|
| CN | 1642897 A | 7/2005 |
| CN | 101745398 A | 6/2010 |
| CN | 102513137 A | 6/2012 |
| JP | 2008530150 A | 8/2008 |
| JP | 2011522015 A | 7/2011 |
| JP | 2012-157794 A | 8/2012 |
| KR | 10-0835476 B1 | 5/2008 |
| KR | 10-2009-0057612 A | 6/2009 |
| KR | 10-1002761 B1 | 12/2010 |
| KR | 10-2012-0093853 A | 8/2012 |
| KR | 10-2012-0117255 A | 10/2012 |
| KR | 10-2013-0109662 A | 10/2013 |

OTHER PUBLICATIONS

Y. Cheng et al., Catalysis Today, 151 (2010) pp. 266-270; "The different impacts of SO 2 and SO 3 on CU/zeolite SCR catalysts." The 108th Symposium on Catalysis Symposium Part A, Catalysis Society, Sep. 13, 2011, P.407, 2G06, ISSN: 1343-9936.

* cited by examiner

*Primary Examiner* — Sikarl Witherspoon
(74) *Attorney, Agent, or Firm* — Dentons US LLP

(57) ABSTRACT

The present invention relates to a catalyst for glycerin dehydration, a preparation method thereof, and a preparation method of acrolein. The catalyst for glycerin dehydration exhibits a high glycerin conversion ratio, minimizes by-product formation to improve acrolein selectivity, and also maintains high catalytic activity during reaction.

7 Claims, No Drawings

CATALYST FOR GLYCERIN DEHYDRATION, PREPARATION METHOD THEREOF, AND PREPARATION METHOD OF ACROLEIN

This application is a National Stage Entry of International Application No. PCT/KR2014/011079, filed on Nov. 18, 2014, and claims the benefit of Korean Application No. 10-2013-0139992, filed on Nov. 18, 2013, and Korean Application No. 10-2014-0160193, filed on Nov. 17, 2014, all of which are hereby incorporated by reference in their entirety.

TECHNICAL FIELD

The present invention relates to a catalyst for glycerin dehydration, a preparation method thereof, and a preparation method of acrolein, and more particularly, to a catalyst for glycerin dehydration which allows glycerin dehydration with a high conversion ratio and reaction yield, minimizes by-product formation to improve acrolein selectivity, and also maintains high catalytic activity during reaction, a preparation method thereof, and a preparation method of acrolein.

BACKGROUND OF ART

Acrolein is a simple unsaturated aldehyde compound which includes incomplete reactive groups to have high reactivity, and is used as a major intermediate for synthesis of numerous chemicals. In particular, acrolein has been widely used as an intermediate for synthesis of acrylic acids, acrylic acid esters, superabsorbent polymers, animal feed supplements, or food supplements.

Such acrolein has been mainly prepared by selective gas-phase oxidation of a starting material, propylene, which is obtained during petroleum cracking with atmospheric oxygen. However, as fossil fuels have been reduced and environmental problems such as greenhouse effect have emerged, many studies have been conducted to develop a method of preparing acrolein using non-fossil fuel-based renewable materials.

Therefore, glycerin, which is a natural by-product obtained from biodiesel production has received much attention as a raw material for acrolein preparation. In particular, growth of biodiesel production increases the glycerin market, and industrial application of glycerin has been studied due to its low price.

For example, a method of obtaining acrolein by glycerin dehydration in the presence of a catalyst is known, in which an acid catalyst such as a zeolite, a phosphate, and tungstophosphoric acid ($H_3PW_{12}O_{40}$) is used.

However, the previous catalysts used for the preparation of acrolein produce by-products such as hydroxyacetone, hydroxy propanone, propane aldehyde, acetaldehyde, acetone, and polycondensation products of glycerin, and thus there are limitations in their use for the preparation of acrolein with high purity.

Accordingly, there is a demand to develop a highly active catalyst system capable of minimizing by-product formation to increase selectivity and purity of acrolein and improving a conversion ratio and reaction yield of glycerin.

DETAILED DESCRIPTION OF THE INVENTION

Technical Problem

An object of the present invention is to provide a catalyst for glycerin dehydration, which allows glycerin dehydration with a high conversion ratio and reaction yield, minimizes by-product formation to improve acrolein selectivity, and also maintains high catalytic activity during reaction.

Another object of the present invention is to provide a preparation method of the catalyst for glycerin dehydration.

Still another object of the present invention is to provide a preparation method of acrolein using the catalyst for glycerin dehydration.

Technical Solution

The present invention provides a catalyst for glycerin dehydration including a mixture of a metal sulfate and a zeolite.

Further, the present invention provides a preparation method of the catalyst for glycerin dehydration, including the step of physically mixing a metal sulfate and a zeolite.

Furthermore, the present invention provides a preparation method of acrolein, including the step of reacting glycerin in the presence of the catalyst for glycerin dehydration.

Hereinafter, a catalyst for glycerin dehydration, a preparation method thereof, and a preparation method of acrolein according to specific embodiments of the present invention will be described in more detail.

As used herein, the term "glycerin dehydration" means an overall process by which water is separated from a glycerin molecule or between glycerin molecules. Glycerin may be converted to acrolein via this glycerin dehydration.

According to an embodiment of the present invention, a catalyst for glycerin dehydration including a mixture of a metal sulfate and a zeolite is provided.

The present inventors recognized that in the known method of preparing acrolein by gas-phase oxidation of a starting material, propylene has limitations of reduced fossil fuel stocks and environmental problems such as the greenhouse effect, and therefore they have studied on a method of preparing acrolein using environmentally friendly and renewable raw materials. As a result, they found that glycerin dehydration can be performed in the presence of a catalyst including a mixture of a metal sulfate and a zeolite so as to prepare acrolein with a high yield and a high conversion ratio while minimizing by-product formation, thereby completing the present invention.

In particular, the catalyst for glycerin dehydration is in the form of a simple mixture of a sulfate of a metal such as copper, iron, zinc, calcium, or cobalt, and a zeolite. Thus, although its preparation is simple and easy, the catalyst is able to remarkably reduce by-product formation to increase acrolein selectivity, compared to the catalysts for glycerin dehydration or acrolein preparation previously used.

The metal sulfate may include one or more metals selected from the group consisting of copper, iron, zinc, calcium, and cobalt, and may also be a mixture of metal sulfates containing different metals. That is, the catalyst for glycerin dehydration may include one or more metal sulfates containing one or more metals selected from the group consisting of copper, iron, zinc, calcium, and cobalt, together with a zeolite.

The metal sulfate shows a property of having high acidic strength in glycerin dehydration, and thus it is possible to prepare a large amount of acrolein with a high conversion ratio. In addition, the metal sulfate may function as a major active phase that directly affects the catalytic activity. In particular, since the metal sulfate contains one or more selected from the group consisting of copper, iron, zinc, calcium, and cobalt, it exhibits excellent catalytic activity and lower carbon deposition, thereby showing a favorable effect on glycerin dehydration for acrolein preparation, compared to a metal sulfate containing Mg, Al, K, Zr, etc.

Specifically, the metal sulfate may be $CuSO_4$, $Fe_2(SO_4)_3$, $ZnSO_4$, $CaSO_4$, $CoSO_4$, or a mixture thereof.

The zeolite included in the catalyst for glycerin dehydration of an embodiment controls cation exchange or $SiO_2/Al_2O_3$ composition to control acidic strength of the catalyst. Therefore, formation of by-products such as hydroxyacetone may be reduced to achieve high acrolein selectivity. Specifically, the zeolite may be β-Zeolite, ZSM-5, or a mixture thereof.

Meanwhile, in the catalyst for glycerin dehydration, the metal sulfate and the zeolite may exist in the form of a mixture. That is, the zeolite is not used as a support as in the known catalysts, but exists in the form of a simple mixture by physically mixing with the metal sulfate without chemical reaction. As such, when the metal sulfate and the zeolite exist as the mixture, the catalyst exhibits more stable catalytic activity and lower carbon deposition than other catalysts, thereby preparing the acrolein with higher activity and conversion ratio.

In the catalyst for glycerin dehydration, the metal sulfate and the zeolite may be included at a weight ratio of 1:3 to 10:1, and preferably 1:2 to 5:1. Since the metal sulfate may be a mixture of different metal sulfates, the mixing ratio may be one of a total content of two or more kinds of metal sulfates to the zeolite.

In the catalyst, if the metal sulfate includes two kinds of sulfates containing different metals, a weight ratio of the first metal sulfate and the second metal sulfate may be 1:1 to 1:5, and preferably 1:1 to 1:3. In this regard, the first metal compound which is included at a smaller amount than the second metal sulfate may be copper sulfate ($CuSO_4$). Since copper sulfate has strong acidity, higher activity may be provided for the catalyst for glycerin dehydration, and the acrolein may be prepared with high selectivity.

In addition, the second metal sulfate may function to increase the low boiling point of the copper sulfate and to act as a supply source of a sulfate, thereby providing a favorable effect on the reaction activity, and examples thereof may include $Fe_2(SO_4)_3$, $ZnSO_4$, $CaSO_4$, $CoSO_4$, etc.

According to another embodiment of the present invention, a preparation method of a catalyst for glycerin dehydration including the step of physically mixing a metal sulfate and a zeolite is provided.

This preparation method may be used to provide the above-described catalyst for glycerin dehydration of an embodiment of the present invention. As described above, this catalyst is a simple mixture of a metal sulfate and a zeolite. Thus, although its preparation is simple and easy, the catalyst is able to minimize by-product formation in glycerin dehydration, thereby preparing acrolein with high selectivity.

The metal sulfate may include one or more metals selected from the group consisting of copper, iron, zinc, calcium, and cobalt, and examples thereof may include $CuSO_4$, $Fe_2(SO_4)_3$, $ZnSO_4$, $CaSO_4$, $CoSO_4$, and mixtures thereof.

The zeolite may include one or more selected from the group of β-Zeolite, ZSM-5, and a mixture thereof.

Further, the metal sulfate and the zeolite may be physically mixed at a weight ratio of 1:3 to 10:1, and preferably, at a weight ratio of 1:2 to 5:1. Since the metal sulfate may be a mixture of metal sulfates containing different metals, the mixing ratio may be one of a total content of two or more kinds of metal sulfates to the zeolite.

If the metal sulfate includes two kinds of sulfates containing different metals, a weight ratio of the first metal sulfate and the second metal sulfate may be 1:1 to 1:5, and preferably 1:1 to 1:3.

The above description of the catalyst for glycerin dehydration of an embodiment may also be applied to the metal sulfate, the zeolite, and the mixing ratio thereof without limitation.

According to still another embodiment of the present invention, a preparation method of acrolein including the step of reacting glycerin in the presence of the above-described catalyst for glycerin dehydration is provided.

As described above, when the catalyst for glycerin dehydration of an embodiment of the present invention may be used, it is possible to perform glycerin dehydration with high acrolein selectivity, in particular, to minimize by-product formation, compared to use of the previously known catalysts.

The amount of the catalyst for glycerin dehydration may be properly controlled depending on the amount and concentration of the reactant glycerin, and for example, the catalyst may be packed at a weight hourly space velocity of 10 to 300 mmol/h·$g_{cat}$, and preferably, at a weight hourly space velocity of 10 to 100 mmol/h·$g_{cat}$.

Further, the step of reacting glycerin may be performed at a temperature of 200 to 400° C. Since the step of reacting glycerin is an endothermic reaction, the reaction may be preferably performed at a temperature within the above range in order to prepare acrolein with a high conversion ratio and selectivity.

Advantageous Effects

According to the present invention, provided are a catalyst for glycerin dehydration which allows glycerin dehydration with a high conversion ratio and reaction yield, minimizes by-product formation to improve acrolein selectivity, and also maintains high catalytic activity during reaction, a preparation method thereof, and a preparation method of acrolein.

DETAILED DESCRIPTION OF THE EMBODIMENTS

The present invention will be described in more detail with reference to the following examples. However, these examples are for illustrative purposes only, and the invention is not intended to be limited by these examples.

EXAMPLES AND COMPARATIVE EXAMPLES

Preparation of Catalyst for Glycerin Dehydration

Example 1

A $CuSO_4$+B-zeolite-based mixed catalyst was prepared by a physical mixing method, and then used. $CuSO_4$ and B-zeolite were mixed at a weight ratio of 8:2 by the physical mixing method, and then the mixture was pulverized in a mortar until a fine powder was obtained. After molding to a size of about 250 μm, the powder was used as a catalyst for dehydration. The catalyst was not subjected to an additional calcination process.

Example 2

A $CuSO_4$+ZSM-5 mixed catalyst was prepared by a physical mixing method, and then used. $CuSO_4$ and ZSM-5 were mixed at a weight ratio of 8:2 by the physical mixing method, and then the mixture was pulverized in a mortar until a fine powder was obtained. After molding to a size of about 250 µm, the powder was used as a catalyst for dehydration. The catalyst was not subjected to an additional calcination process.

Example 3

A $CuSO_4+Fe_2(SO_4)_3$+B-zeolite mixed catalyst was prepared by a physical mixing method, and then used. $CuSO_4$, $Fe_2(SO_4)_3$, and B-zeolite were mixed at a weight ratio of 1:1.25:4 by the physical mixing method, and then the mixture was pulverized in a mortar until a fine powder was obtained. After molding to a size of about 250 µm, the powder was used as a catalyst for dehydration. The catalyst was not subjected to an additional calcination process.

Example 4

A $CuSO_4+Fe_2(SO_4)_3$+ZSM-5 mixed catalyst was prepared by a physical mixing method, and then used. $CuSO_4$, $Fe_2(SO_4)_3$, and ZSM-5 were mixed at a weight ratio of 1:1.25:4 by the physical mixing method, and then the mixture was pulverized in a mortar until a fine powder was obtained. After molding to a size of about 250 µm, the powder was used as a catalyst for dehydration. The catalyst was not subjected to an additional calcination process.

Example 5

A $CuSO_4+ZnSO_4$+B-zeolite mixed catalyst was prepared by a physical mixing method, and then used. $CuSO_4$, $ZnSO_4$, and B-zeolite were mixed at a weight ratio of 1:1.25:4 by the physical mixing method, and then the mixture was pulverized in a mortar until a fine powder was obtained. After molding to a size of about 250 µm, the powder was used as a catalyst for dehydration. The catalyst was not subjected to an additional calcination process.

Example 6

A $CuSO_4+CaSO_4$+B-zeolite mixed catalyst was prepared by a physical mixing method, and then used. $CuSO_4$, $CaSO_4$, and B-zeolite were mixed at a weight ratio of 1:1.25:4 by the physical mixing method, and then the mixture was pulverized in a mortar until a fine powder was obtained. After molding to a size of about 250 µm, the powder was used as a catalyst for dehydration. The catalyst was not subjected to an additional calcination process.

Example 7

A $CuSO_4+CaSO_4$+ZSM-5 mixed catalyst was prepared by a physical mixing method, and then used. $CuSO_4$, $CaSO_4$, and ZSM-5 were mixed at a weight ratio of 1:1.25:4 by the physical mixing method, and then the mixture was pulverized in a mortar until a fine powder was obtained. After molding to a size of about 250 µm, the powder was used as a catalyst for dehydration. The catalyst was not subjected to an additional calcination process.

Example 8

A $CuSO_4+CoSO_4$+B-zeolite mixed catalyst was prepared by a physical mixing method, and then used. $CuSO_4$, $CoSO_4$, and B-zeolite were mixed at a weight ratio of 1:1.25:4 by the physical mixing method, and then the mixture was pulverized in a mortar until a fine powder was obtained. After molding to a size of about 250 µm, the powder was used as a catalyst for dehydration. The catalyst was not subjected to an additional calcination process.

Comparative Example 1

$CuSO_4$ which was purchased from Daejung Chemical & Metal Co. was pulverized in a mortar until a fine powder was obtained. After molding to a size of about 250 µm, the powder was used as a catalyst for dehydration. The catalyst was not subjected to an additional calcination process.

Comparative Example 2

$Fe_2(SO_4)_3$ which was purchased from Daejung Chemical & Metal Co. was pulverized in a mortar until a fine powder was obtained. After molding to a size of about 250 µm, the powder was used as a catalyst for dehydration. The catalyst was not subjected to an additional calcination process.

Comparative Example 3

$ZnSO_4$ which was purchased from Daejung Chemical & Metal Co. was pulverized in a mortar until a fine powder was obtained. After molding to a size of about 250 µm, the powder was used as a catalyst for dehydration. The catalyst was not subjected to an additional calcination process.

Comparative Example 4

B-zeolite which was purchased from Zeolite was pulverized in a mortar until a fine powder was obtained. After molding to a size of about 250 µm, the powder was used as a catalyst for dehydration. The catalyst was subjected to calcination under an air atmosphere at 700° C. for 5 hours.

Comparative Example 5

ZSM-5 which was purchased from Zeolite was pulverized in a mortar until a fine powder was obtained. After molding to a size of about 250 µm, the powder was used as a catalyst for dehydration. The catalyst was subjected to calcination under an air atmosphere at 700° C. for 5 hours.

Comparative Example 6

For $CuSO_4+SiO_2$, $CuSO_4$ was purchased from Daejung Chemical & Metal Co. and sylopol 925X was used as $SiO_2$, and they were mixed at a weight ratio of 2:8. The mixture was pulverized in a mortar until a fine powder was obtained. After molding to a size of about 250 µm, the powder was used as a catalyst for dehydration. The catalyst was not subjected to an additional calcination process.

Comparative Example 7

As $H_3PW_{12}O_{40}$, 12-tungsto(VI) phosphoric acid n-hydrate (99%) was purchased from Wako Co., and the catalyst was subjected to calcination under an air atmosphere at 300° C. for 4 hours. After calcination, the catalyst was molded to a size of about 250 µm, and used as a catalyst for dehydration.

Comparative Example 8

For $BPO_4$, $H_3BO_3$ and $H_3PO_4$ were used and mixed at a molar ratio of 1:1 using distilled water as a solvent. Then, the mixture was heated at 60° C. to remove water, and the obtained powder was dried in an oven at 100° C. overnight and subjected to calcination under an air atmosphere at 700° C. for 4 hours. After calcination, the catalyst was molded to a size of about 250 μm, and used as a catalyst for dehydration.

An HTS (high-throughput screening) facility which was manufactured to evaluate performances using a small amount of the catalyst prepared in examples or comparative examples in a short time under conditions given in the following Table 1 was used to prepare acrolein from glycerin, and the product was subjected to in-situ GC analysis to calculate conversion ratio, selectivity, and yield. The conversion ratio of glycerin and selectivity of acrolein are given in the following Tables 2 and 3.

Here, the conversion ratio of glycerin represents a ratio of glycerin to converted compounds, and the selectivity of acrolein represents a ratio of acrolein to the converted compounds.

Further, comparative selectivity 1 represents a comparison of hydroxyacetone selectivity to acrolein selectivity, and comparative selectivity 2 represents a comparison of by-product selectivity to acrolein selectivity. In comparative selectivity 1, hydroxyacetone is a major by-product in glycerin dehydration. In comparative selectivity 2, the by-product includes hydroxyacetone, aryl alcohol, acetol, propionic acid, 1,2-propanediol, 1,3-propanediol, or cyclic acetal compounds produced by dimer dehydration between glycerin molecules or acetol and glycerin.

TABLE 1

Conditions for Glycerin Dehydration

| | |
|---|---|
| Reaction temperature | 280° C. |
| Reaction pressure | 1 atm |
| Feed rate of reactant | 3.5 ml/h |
| Reaction time | 1 h |
| Glycerin concentration | 28.08 wt % |
| WHSV (weight hourly space velocity) | 113.03 mmol/(h · $g_{cat}$) |
| Catalyst amount | 0.1 g |

TABLE 2

Chemical Formula of Catalysts Prepared in Examples and Comparative Examples, Glycerin Conversion Ratio, and Selectivity

| Example | Chemical Formula | Glycerin conversion ratio (%) | Acrolein selectivity (%) |
|---|---|---|---|
| Example 1 | $CuSO_4$ + B-zeolite | 25.7 | 15.3 |
| Example 2 | $CuSO_4$ + ZSM-5 | 25.9 | 27.7 |
| Example 3 | $CuSO_4$ + $Fe_2(SO_4)_3$ + B-zeolite | 22.4 | 28.4 |
| Example 4 | $CuSO_4$ + $Fe_2(SO_4)_3$ + ZSM-5 | 16.3 | 25.0 |
| Example 5 | $CuSO_4$ + $ZnSO_4$ + B-zeolite | 19.4 | 20.3 |
| Example 6 | $CuSO_4$ + $CaSO_4$ + B-zeolite | 23.2 | 21.7 |
| Example 7 | $CuSO_4$ + $CaSO_4$ + ZSM-5 | 31.0 | 24.2 |
| Example 8 | $CuSO_4$ + $CoSO_4$ + B-zeolite | 22.5 | 18.8 |
| Comparative Example 1 | $CuSO_4$ | 18.7 | 20.1 |
| Comparative Example 2 | $Fe_2(SO_4)_3$ | 2.8 | 10.1 |
| Comparative Example 3 | $ZnSO_4$ | 4.9 | 15.0 |
| Comparative Example 4 | B-zeolite | 30.8 | 16.0 |
| Comparative Example 5 | ZSM-5 | 5.4 | 18.8 |
| Comparative Example 6 | $CuSO_4$ + $SiO_2$ | 13.6 | 22.6 |
| Comparative Example 7 | $H_3PW_{12}O_{40}$ | 7.6 | 7.1 |
| Comparative Example 8 | $BPO_4$ | 19.6 | 18.5 |
| Comparative Example 9 | $Fe_x(PO_4)_y$ | 3.9 | 7.8 |

TABLE 3

Selectivity and Comparative Selectivity of Hydroxyacetone

| Example | Hydroxyacetone selectivity (%) | *Comparative selectivity 1 | **Comparative selectivity 2 |
|---|---|---|---|
| Example 1 | 15.3 | 0.9 | 3.9 |
| Example 2 | 14.6 | 0.5 | 1.9 |
| Example 3 | 9.7 | 0.3 | 1.5 |
| Example 4 | 19.8 | 0.8 | 2.2 |
| Example 5 | 18.8 | 0.9 | 2.9 |
| Example 6 | 15.8 | 0.7 | 2.9 |
| Example 7 | 15.6 | 0.7 | 2.1 |
| Example 8 | 20.8 | 1.1 | 3.3 |
| Comparative Example 1 | 20.9 | 1.0 | 3.3 |
| Comparative Example 2 | 29.8 | 3.0 | 8.1 |
| Comparative Example 3 | 22.6 | 1.5 | 4.4 |
| Comparative Example 4 | 17.7 | 1.1 | 4.4 |
| Comparative Example 5 | 25.1 | 1.3 | 3.9 |
| Comparative Example 6 | 20.7 | 0.9 | 2.6 |
| Comparative Example 7 | 25.1 | 3.5 | 9.1 |
| Comparative Example 8 | 38.7 | 2.1 | 3.9 |
| Comparative Example 9 | 7.6 | 1.0 | 8.9 |

*Comparative selectivity 1 = hydroxyacetone selectivity/acrolein selectivity
**Comparative selectivity 2 = by-product selectivity/acrolein selectivity As shown in Tables 2 and 3, when the catalysts including the mixture of the metal sulfate and the zeolite of the examples were used to react glycerin, a high glycerin conversion ratio and acrolein selectivity were observed, compared to a single use of a metal sulfate or a zeolite in comparative examples, and comparative selectivity 1 or 2 which is a ratio of by-product selectivity to selectivity of acrolein which is a main product as a target of the reaction was low, compared to use of the catalysts of the comparative examples.

In particular, the catalysts prepared in the examples exhibited remarkably high glycerin conversion ratio and low comparative selectivity, compared to those of the comparative examples. Thus, the catalyst for glycerin dehydration of an embodiment is used to prepare acrolein with high selectivity and high purity and to inhibit formation of by-products such as hydroxyacetone.

The invention claimed is:

1. A preparation method of acrolein, comprising a step of reacting glycerin in the presence of a catalyst for glycerin dehydration,
   wherein the catalyst comprises a mixture of a metal sulfate and a zeolite, and wherein the metal sulfate and the zeolite are included at a weight ratio of 1:3 to 10:1.

2. The preparation method of claim 1, wherein the metal sulfate includes one or more metals selected from the group consisting of copper, iron, zinc, calcium, and cobalt.

3. The preparation method of claim 1, wherein the metal sulfate includes one or more selected from the group consisting of $CuSO_4$, $Fe_2(SO_4)_3$, $ZnSO_4$, $CaSO_4$, and $CoSO_4$.

4. The preparation method of claim 1, wherein the zeolite includes one or more selected from the group consisting of β-zeolite and ZSM-5.

5. The preparation method of claim 1, wherein the metal sulfate includes two kinds of sulfates containing different metals at a weight ratio of 1:1 to 1:5.

6. The preparation method of claim 1, wherein the catalyst for glycerin dehydration is packed at a weight hourly space velocity of 10 to 300 mmol/h·$g_{cat}$.

7. The preparation method of claim 1, wherein the step of reacting glycerin is performed at a temperature of 200 to 400° C.

* * * * *